United States Patent [19]

Wilson et al.

[11] 4,205,065

[45] May 27, 1980

[54] NON-YELLOWING COMPOSITIONS CONTAINING HEXAMETHYLENETETRAMINE 1,3-DICHLOROPROPENE SALTS

[75] Inventors: David A. Wilson, Richwood; Avis L. McCrary, Lake Jackson, both of Tex.

[73] Assignee: The Dow Chemical Company, Midland, Mich.

[21] Appl. No.: 4,096

[22] Filed: Jan. 17, 1979

[51] Int. Cl.² .................. A61K 31/78; A01N 9/22; A61K 31/53; A01N 9/00
[52] U.S. Cl. ..................... 424/81; 424/126; 424/164; 424/175; 424/249
[58] Field of Search ............... 424/126, 164, 175, 81, 424/249

[56] References Cited

U.S. PATENT DOCUMENTS

| | | | |
|---|---|---|---|
| 3,532,657 | 10/1970 | Dick et al. | 260/29.2 |
| 3,766,063 | 10/1973 | Blankenhorn | 424/175 |
| 3,908,009 | 9/1975 | Polemenakos et al. | 424/249 |

*Primary Examiner*—Donald B. Moyer
*Attorney, Agent, or Firm*—Joyce P. Hill

[57] ABSTRACT

A novel composition of matter comprising a color-inhibiting additive, such as sodium bisulfite, and cis-1-(3-chloroallyl)-3,5,7-triaza-1-azoniaadamantane chloride or the cis-, trans- mixtures of 1-(3-chloroallyl)-3,5,7-triaza-1-azoniaadamantane chloride, is a non-yellowing antimicrobial formulation suitable for the preservation of aqueous organic mixtures such as emulsions, dispersions, latexes and solutions. The color-inhibiting agent may be added as a solid or as an aqueous solution wherein the weight ratio of adamantane to additive is from about 1:0.01 to about 1:4.

15 Claims, No Drawings

NON-YELLOWING COMPOSITIONS CONTAINING HEXAMETHYLENETETRAMINE 1,3-DICHLOROPROPENE SALTS

BACKGROUND OF THE INVENTION

Products prepared by reacting hexamethylenetetramine with 1,3-dichloropropene are well-known and successful antimicrobial agents; U.S. Pat. No. 3,228,829. One product, cis-1-(3-chloroallyl)-3,5,7-triaza-1-azoniaadamantane chloride, commercially available as DOWICIL ® (Registered trademark of The Dow Chemical Company) 200 and hereinafter referred to as "cis-compound" is used primarily in cosmetic and allied formulations. Another product, cis-,trans- mixtures of 1-(3-chloroallyl)-3,5,7-triaza-1-azoniaadamantane chloride, commercially available under the DOWICIL ® tradename, containing from about 50 to 99.5 percent cis-isomer and about 50 to 0.5 percent trans-isomer, is hereinafter referred to as "cis-,trans-compound". The cis-,trans-compound is used in commercial formulations such as, emulsifiable metal-cutting fluids; latex and emulsion paints; liquid floor polishes and floor waxes; glues and adhesives; coatings, sizings and printing colors for pulp and paper; and finishing solutions and printing pastes used by textile producers.

Although well-known and successful as antimicrobial agents, the cis- and cis-,trans-compounds may cause yellowing of the treated formulations. This yellowing seems to occur quickly, requiring only a few days to develop.

Certain amine compounds were found to inhibit color formation in aqueous solutions containing the cis- and cis-,trans-compounds. Polemenakos and Langer in U.S. Pat. No. 3,908,009 teach the use of amine compounds to stabilize solutions against discoloration. However it was found that the amines that work well in aqueous solutions did not work in the latex systems. It is desirable to prevent the yellowing of most compositions containing the aforesaid antimicrobial agents, especially in areas such as the latex and cosmetic industries.

This invention provides a novel composition of matter which utilizes the effective antimicrobial properties of the cis-compound and cis-,trans-compound and affords a non-yellowing formulation.

SUMMARY OF THE INVENTION

A novel composition of matter consisting essentially of cis- or cis-,trans-compound and a color-stabilizing agent, such as sodium bisulfite, is useful as a non-yellowing, antimicrobial agent in aqueous dispersions, solutions, etc. which are subject to attack by putrefactive bacteria. The non-yellowing, antimicrobial agent of this invention, is especially useful in the cosmetic and latex industries and prevents the loss of useful properties, foul odors, slime formation, and the possibility of skin infections in persons handling aqueous systems preserved against microbial decomposition.

The color-stabilizing additive is a reducing agent selected from alkali metal, alkaline earth metal, amine or ammonium sulfites or bisulfites; inorganic hydrides; or hydroxylamine and acid salts thereof. The additives may be added as a solid or as an aqueous solution. The preferred weight ratio of cis- or cis-,trans-compound to additive is from about 1:0.01 to about 1:4.

DETAILED DESCRIPTION OF THE INVENTION

A color-stabilizing additive in combination with a cis-compound or a cis-,trans-compound forms a novel composition of matter having non-yellowing, antimicrobial properties.

In making cis-,trans-compound, the hexamethylenetetramine is reacted with a commercial mixture containing cis- and trans-1,3-dichloropropene and inert material. While in the case of cis-compound, the cis-1,3-dichloropropene is separated from the above mixture and reacted with hexamethylenetetramine to give cis-compound. A method for the preparation of this cis-compound and the cis-,trans-compound is found in U.S. Pat. No. 3,228,829 and is incorporated herein by reference.

Compounds from the known class of reducing agents are particularly suitable color-stabilizing additives in the instant invention.

The reducing agent may be selected from alkali metal, alkaline earth metal, amine or ammonium sulfites or bisulfites; inorganic hydrides; or hydroxylamine and acid salts thereof. Following are more compounds which are illustrative reducing agents: sodium sulfite, sodium bisulfite, potassium sulfite, potassium bisulfite, lithium sulfite, lithium bisulfite, magnesium sulfite, magnesium bisulfite, calcium bisulfite, ammonium sulfite, ammonium bisulfite, sodium borohydride, lithium aluminum hydride, lithium borohydride, hydroxylamine hydrochloride, hydroxylamine, hydroxylamine sulfate and the like. The preferred color-inhibiting additives are sodium sulfite, sodium borohydride, sodium bisulfite, and hydroxylamine hydrochloride.

The color-stabilizing additive or reducing agent may be added as a solid or as an aqueous solution. The additive may also comprise a mixture of the suitable reducing agents. The preferred weight ratio of cis- or cis-,trans-compound to additive is from about 1:0.01 to about 1:4, most preferably 1:1. Generally a 1:1 (additive/cis-compound) weight ratio is required for inhibiting discoloration of compositions containing cis-compound using hydroxylamine hydrochloride and sodium bisulfite. Greater ratios can be used if desired. Lower ratios may be effective depending on the system used. The amount of $NaBH_4$ needed to control color formation was found to be much smaller. For example a 1:10 (additive/cis-compound) weight ratio was found to be sufficient for color stabilization. Larger amounts of $NaBH_4$ can also be used.

In the preparation of the novel composition of matter of this invention, the color-stabilizing additive may be incorporated into the cis-compound or cis-,-trans-compound by any conventional means suitable for mixing powders, including stirring, blending, use of a mortar and pestle, etc. Advantageously, the color-stabilizing additive is added to an aqueous solution or formulation as soon as it is made, and, for best results, as soon as possible after the antimicrobial, cis- or cis-,trans-compounds are added to the water-containing formulation. In the aforesaid manner, the novel composition of matter of this invention is generated in situ. If desired, the aqueous phase may be buffered to an appropriate pH, e.g., between 6 and 8. However, buffering is not essential to the successful use of the novel composition of this invention.

Both cis-compound and cis-,trans-compound containing a color-stabilizing additive may be used in clear or light-colored formulations containing a continuous or discontinuous aqueous phase wherein the antimicrobial is present primarily in the aqueous phase. The color stabilizing additive is used to prevent undesirable yellowing on aging. The amount of cis- or cis-,trans-compound used as a preservative may vary from 0.01 to about 20 weight percent based on the total weight of the water-containing formulation. Formulations which are known to benefit from the use of antimicrobial agents are emulsifiable metal-cutting fluids; latex and emulsion paints; liquid floor polishes and floor waxes; glues and adhesives; coatings, sizings and printing colors for pulp and paper; finishing solutions and printing pastes used by textile producers; and cosmetics. In practice, the stabilized compositions of the present invention are prepared by merely adding the color-stabilizing additive to the cis- or cis-,trans-compound formulation in the amounts indicated above and mixing thoroughly by conventional means.

Generally, the conditions for mixing the novel composition of matter of this invention and aqueous industrial formulations are not temperature or pressure sensitive and room temperatures (i.e., 20° C. to 25° C.) and atmospheric or superatmospheric pressures may be used as a matter of convenience.

The following non-limiting examples clearly illustrate the invention. Unless otherwise specified, parts and percentages are by weight.

EXAMPLE 1

In a glass vessel, at 22° C. an aqueous solution of cis-compound (1 percent by weight) is prepared. The solution is subjected to accelerated aging by placing the vessel containing the solution in a 54° C. water bath. A comparison of yellowing results between cis-compound solutions at ambient temperature (i.e., 20° C.-25° C.) and 54° C. resulted in an approximate aging relationship of 24 hours at 54° C. being equivalent to three weeks at ambient temperature. After 72 hours at 54° C. (9 weeks of aging), the color of the solution was intensely yellow, having increased from a Gardner color of <1 to about 7. The Gardner color is obtained by matching the color of the sample with the appropriate standard tube. Tube numbers 1-8 are based on solutions of potassium chloroplatinate while tube numbers 9-18 are based on solutions of ferric chloride and cobalt chloride. See ASTM Method D1544-58I. The instant example clearly illustrates the intense yellowing that occurs on the aging of an aqueous solution of the cis-compound.

EXAMPLES 2-3

Under similar conditions described in Example 1, cis-compound and an additive are dissolved in water in the quantities shown below. The aqueous, cis-compound/additive solution is aged at 54° C. in a water bath. In Table I, the results using two color-inhibiting additives are summarized after 72 hours (9 weeks aging).

TABLE I

Non-Yellowing Aqueous Compositions

| Ex. No. | Additive | *Amt. of Additive | *Amt. of Cis-Compound | Gardner Color Before | After |
|---|---|---|---|---|---|
| 2 | Sodium borohydride | 1% | 1% | <1 | <1 |
| 3 | Hydroxylamine hydrochloride | 1% | 1% | <1 | <1 |

*Weight percent is based on the total weight of the system.

EXAMPLE 4

Two separate aqueous solutions are prepared as described in Example 1. One solution contained 2 percent cis-compound and 2 percent sodium bisulfite. The other solution contained 2 percent cis-compound and is used as a control. Both solutions are aged at 54° C. for 144 hours (18 weeks). The initial pH is adjusted to 10.0 for both solutions. The comparison shown in Table II below illustrates the effectiveness of the sodium bisulfite ($NaHSO_3$) additive in preventing the yellowing of the aqueous solution.

TABLE II

Effect of $NaHSO_3$ on Yellowing of Aqueous Solution

| Additive | Gardner Color Before | After |
|---|---|---|
| none | <1 | ~7 (intense yellow) |
| sodium bisulfite | <1 | ~2 (faint yellow) |

EXAMPLES 5-6

Aging Study of Latex Systems (75 Percent Vinyl Acetate/25 Percent Butyl Acrylate)

A latex system is prepared by diluting a vinyl acetate/butyl acrylate latex 1:1 with deionized water and adding cis-compound (0.1 weight percent based on latex) and a specified additive. Samples were aged at 54° C. for three weeks and at 75° C. for ten days. The Gardner color standards were not used to monitor the discoloration of the latex systems. A rating of 0-5 was chosen wherein 0 represents white and 5 represents a complete change in hue. This method was found to relate more accurately the color changes that occur in the latex systems. Results of the aging studies are shown in Tables III and IV.

TABLE III

Aging Study of Latex System - 54° C.

| System | Color-Stabilizing Additive* | Color Before | After |
|---|---|---|---|
| latex | | 0 | 0 |
| latex + Cis-Compound | | 0 | 2 |
| latex + Cis-Compound + | $NaBH_4$ | 0 | 0 |
| latex + Cis-Compound + | $NH_2OH \cdot HCl$ | 0 | 0 |
| latex + $NH_4OH$ + Cis-Compound | | 0 | 3 |
| latex + $NH_4OH$ + Cis-Compound + | $NaBH_4$ | 0 | 0 |

*Color-stabilizing additives are 0.1 weight percent based on latex.
**The latex as produced is acidic, but users will normally pH adjust the finished paint to a pH of 8.5-9.0 with an amine such as ammonia.

TABLE IV

Aging Study of Latex System - 75° C.

| System | Color-Stabilizing Additive** | Color Before | Color After |
|---|---|---|---|
| latex + NH₄OH* | | 0 | 2 |
| latex + NH₄OH + Cis-Compound | | 0 | 5 |
| latex + NH₄OH + Cis-Compound + | NH₂OH . HCl (0.1%) | 0 | 0 |
| latex + NH₄OH +Cis-Compound + | NaBH₄ (0.05%) | 0 | 0 |
| latex + NH₄OH + Cis-Compound + | NaBH₄ (0.1%) | 0 | 0 |
| latex + NH₄OH + Cis-Compound + | NaHSO₃ (0.1%) | 0 | 2 |
| latex + NH₄OH + Cis-Compound + | NaHSO₃ (0.5%) | 0 | 1 |

*The latex as produced is acidic, but users will normally pH adjust the finished paint to a pH of 8.5-9.0 with an amine such as ammonia.
**Color-stabilizing additives are expressed as weight percentages based on the latex.

EXAMPLE 7

In this example, yellowing is monitored for amine/cis-compound stabilized latex solutions and aqueous solutions.

The Gardner standards were used to determine the color of the aqueous solutions while the method described in Examples 5-6 is used to monitor discoloration in the latex systems. The aqueous solutions consist of 1 percent cis-compound and 1 percent amine based on the total weight of the solution. The latex systems consist of 0.1 percent cis-compound and 0.1 percent amine based on the weight of the latex.

The aqueous solutions were aged for 72 hours at 54° C. (9 weeks at room temperature). The latex solutions were aged for three weeks at 54° C.

TABLE V

Amine Inhibited Yellowing Study

| Aqueous System | Color Before | Color After |
|---|---|---|
| Cis-Compound in water | <1 | 7 |
| Cis-Compound + diethanolamine in water | <1 | <1 |
| Cis-Compound + 1,3-propanediamine in water | <1 | <1 |
| Cis-Compound + 1,2-propanediamine in water | <1 | <1 |

| Latex System | Color Before | Color After |
|---|---|---|
| latex + Cis-Compound | 0 | 2 |
| latex + Cis-Compound + diethanolamine in water | 0 | 3 |
| latex + Cis-Compound + 1,3-propanediamine in water | 0 | 5 |
| latex + Cis-Compound + 1,2-propanediamine in water | 0 | 5 |

*Gardner color
**Color based on 0=white and 5=complete change in hue.

The above data reveal that certain amine compounds work well in aqueous solutions but do not work in the latex systems.

What is claimed is:

1. A composition of matter having antimicrobial properties which consists essentially of
    (a) cis-1-(3-chloroallyl)-3,5,7-triaza-1-azoniaadamantane chloride; and
as a color-stabilizing additive for the said adamantane in solution, to prevent yellowing of the adamantane solution on aging,
    (b) a reducing agent selected from alkali metal sulfites, alkali metal bisulfites, alkaline earth metal sulfites, alkaline earth metal bisulfites, amine sulfites, amine bisulfites, ammonium sulfites, ammonium bisulfites, inorganic hydrides, hydroxylamine, hydroxylamine acid salts and mixtures thereof, wherein the weight ratio of (a) to (b) is from 1:0.01 to 1:4.

2. An aqueous solution of the composition of claim 1, said aqueous solution containing a bactericidal amount, from about 0.01 to about 20 weight percent of said adamantane.

3. An aqueous formulation of the composition of claim 1 wherein the aqueous formulation contains from about 0.01 to about 5.0 weight percent of cis-1-(3-chloroallyl)-3,5,7-triaza-1-azoniaadamantane chloride based on the total weight of the water-containing formulation.

4. A latex formulation of the composition of claim 1, said latex containing a bactericidal amount, from about 0.01 to about 1.0 weight percent of said adamantane.

5. A latex formulation of the composition of claim 4, wherein said latex is 75 percent vinyl acetate/-25 percent butyl acrylate.

6. A composition of matter having antimicrobial properties which consists essentially of
    (a) cis-,trans-mixture of 1-(3-chloroallyl)-3,5,7-triaza-1-azoniaadamantane chloride, and
as a color-stabilizing agent for the said isomeric adamantane mixture in solution, to prevent yellowing of the adamantane solution on aging,
    (b) a reducing agent selected from alkali metal sulfites, alkali metal bisulfites, alkaline earth metal sulfites, alkaline earth metal bisulfites, amine sulfites, amine bisulfites, ammonium sulfites, ammonium bisulfites, inorganic hydrides, hydroxylamine, hydroxylamine acid salts and mixtures thereof, wherein the weight ratio of (a) to (b) is from 1:0.01 to 1:4.

7. A composition as defined in claim 6 wherein the mixture of cis-,trans-isomer is independently 50 to 99.5 percent cis-isomer and 50 to 0.5 percent trans-isomer.

8. An aqueous solution of the composition of claim 6, said aqueous solution containing a bactericidal amount, from about 0.01 to about 20 weight percent of said isomeric adamantane mixture.

9. An aqueous formulation of the composition of claim 6, said aqueous material containing a bactericidal amount, from about 0.01 to about 0.1 weight percent of said isomeric adamantane mixture.

10. A latex formulation comprising the composition of claim 6 wherein said latex is 75 percent vinyl acetate/25 percent butyl acrylate.

11. A process for inhibiting yellowing of a solution containing a bactericidal amount of cis-1-(3-chloroallyl)-3,5,7-triaza-1-azoniaadamantane chloride comprising adding to said adamantane solution a color-stabilizing additive selected from the group consisting of sodium bisulfite, sodium sulfite, sodium borohydride and hydroxylamine hydrochloride wherein the weight ratio of adamantane to additive is from 1:0.01 to 1:4.

12. The process of claim 11 wherein the color-stabilizing additive is present in an amount about equal to the weight of the bactericidal adamantane.

13. A process for inhibiting yellowing of a formulation containing a bactericidal amount of a cis-,trans-mixture of 1-(3-chloroallyl)-3,5,7-triazia-1-azonia-adamantane chloride comprising adding to said adamantane solution a color-stabilizing additive selected from the group consisting of sodium bisulfite, sodium sulfite, sodium borohydride and hydroxylamine hydrochloride wherein the weight ratio of adamantane to additive is from 1:0.01 to 1:4.

14. The process of claim 13 wherein the color-stabilizing additive is present in an amount about equal to the weight of the bactericidal adamantane.

15. A process for inhibiting yellowing of a vinyl acetate latex containing 0.1–0.5 percent cis-1-(3-chloroallyl)-3,5,7-triaza-1-azoniaadamandate chloride, based on weight of latex, comprising adding sodium bisulfite in an amount about equal to the weight of said adamantane at temperatures of from about 20° C. to about 25° C.

* * * * *

UNITED STATES PATENT AND TRADEMARK OFFICE
CERTIFICATE OF CORRECTION

PATENT NO. : 4,205,065
DATED : May 27, 1980
INVENTOR(S) : David A. Wilson and Avis L. McCrary It is certified that error appears in the above-identified patent and that said Letters Patent are hereby corrected as shown below:

Column 3, line 47, delete "Method D1544-58I" and insert --Method D1544-58T--.

Column 4, line 62, after "latex + Cis-Compound + $NH_2OH \cdot HCl$" insert on a new line --latex + $NH_4OH$**    0    1--.

Column 5, line 39, delete "Color" and insert --Color*--.

Column 5, line 45, delete "Color" and insert --Color**--.

Column 6, line 48, delete "0.1" and insert --1.0--.

Signed and Sealed this

Fourteenth Day of October 1980

[SEAL]

Attest:

SIDNEY A. DIAMOND

Attesting Officer

Commissioner of Patents and Trademarks